United States Patent [19]

Weinberger

[11] Plant 4,915

[45] Nov. 2, 1982

[54] NECTARINE TREE

[75] Inventor: John H. Weinberger, Fresno, Calif.

[73] Assignee: Superior Farming Company, Bakersfield, Calif.

[21] Appl. No.: 259,801

[22] Filed: May 4, 1981

[51] Int. Cl.[3] ..... A01H 5/03

[52] U.S. Cl. ..... Plt./41

[58] Field of Search ..... Plt./41

*Primary Examiner*—Robert E. Bagwill

*Attorney, Agent, or Firm*—Roger B. Webster

[57] ABSTRACT

A nectarine tree which is medium size, medium vigorous, upright-spreadng, dense, and round-topped; foliated with medium size, ovate, lanceolate, acutely pointed, smooth, medium thick, medium green leaves having a crenate margin, a petiole of medium length and thickness, and medium size, irregularly alternate, green, reniform glands positioned on petiole and base of blade; blooms from buds medium in size and length, plump, appressed, and pubescent; the flowers, of medium season, being large and pink; and the tree is a regular and productive bearer of large, uniform, symmetrical, globose-slightly ovoid, freestone fruit having yellow skin blushed with red, yellow flesh streaked with red, and a brown stone.

1 Drawing Figure

BACKGROUND OF THE VARIETY

1. Field of the Invention.

In the conduct of an extensive plant breeding program — on behalf of a commercial farming company, and in such company's experimental orchard located near Fresno, Fresno County, Calif. — I have originated a substantial number of new and distinct varieties of fruit trees, and which include the present variety of nectarine tree.

2. Classification of the Variety.

The present variety of nectarine tree is embraced by Class 41, Plants, of the U.S. Patent Office MANUAL OF CLASSIFICATION.

3. Prior Varieties.

Among existing varieties of nectarine trees which are known to me, and mentioned herein, is the Late Le Grand (U.S. Plant Pat. No. 1,035).

ORIGIN OF THE VARIETY

The present variety of nectarine tree was originated by me as an open-pollinated seedling of a late-ripening, unnamed, seedling nectarine tree. A number of such seedlings were grown to fruition, in the aforesaid experimental orchard, under careful and continuing observation by me; the present variety being a selection of one of such open-pollinated seedlings.

ASEXUAL REPRODUCTION OF THE VARIETY

Asexual reproduction of the variety was successfully accomplished, under my direction and in the aforesaid experimental orchard, by budding; such asexual reproductions, in maturity, having run true to the original tree in all respects.

SUMMARY OF THE VARIETY

The present variety of nectarine tree is, characteristically, of medium size, medium vigorous, upright-spreading, dense, and round-topped; foliated with medium size, ovate, lanceolate, acutely pointed, smooth, medium thick, medium green leaves having a crenate margin, a petiole of medium length and thickness, and medium size, irregularly alternate, green, reniform glands positioned on petiole and base of blade; blooms from buds medium in size and length, plump, appressed, and pubescent; the flowers, of medium season, being large and pink; and the tree is a regular and productive bearer of large, uniform, symmetrical, globose-slightly ovoid, freestone fruit having yellow skin blushed with red, yellow flesh streaked with red, and a brown stone.

The present variety of nectarine tree is further, and more particularly, characterized by late-ripening fruit — as described — which is freestone in comparison, for example, to the Late Le Grand and which — along with many other late-ripening nectarines — bears clingstone fruit; the fruit of the present variety ripening approximately with the Late Le Grand.

The present variety of nectarine tree is still further characterized by highly colored, late-ripening, freestone fruit of the best eating quality; the flavor being excellent, and slightly acid.

BRIEF DESCRIPTION OF THE DRAWING

The drawing is an illustration, by photographic reproduction in color, of a twig with leaves, and separate fruit; one fruit being half cut away to expose the flesh and stone.

DESCRIPTION OF THE VARIETY

The botanical details of this new and distinct variety of nectarine tree — with color definitions (except those in common color terms) referenced to Plochere Color System (in book form) — are as follows:

Tree:
- *Size.*—Medium.
- *Vigor.*—Medium.
- *Growth.*—Upright-spreading.
- *Density.*—Dense.
- *Form.*—Round-topped.
- *Production.*—Productive.
- *Bearing.*—Regular bearer.

Trunk:
- *Size.*—Medium.
- *Texture.*—Medium.

Branches:
- *Size.*—Medium.
- *Texture.*—Medium.

*Color.*—New wood: Green. Dull. Mature wood: Brown.

Leaves:

*Size.*—Medium. Average length — 16.7 cm. Average width — 3.9 cm.

*Form.*—Ovate. Lanceolate. Acutely pointed.

*Thickness.*—Medium.

*Color.*—Medium green.

*Texture.*—Smooth.

*Margin.*—Crenate.

*Petiole.*—Medium length. Medium thickness.

*Glands.*—Average number — 3. Alternate — irregular. Medium size. Reniform. Green. Positioned on petiole near base of blade, and on the latter.

*Stipules.*—Shed as leaves mature.

Flower buds:

*Size.*—Medium.

*Length.*—Medium.

*Form.*—Plump. Appressed. Pubescent.

Flowers:

*Date of full bloom.*—Mar. 8th, 1980. Medium, as compared with other varieties.

*Size.*—Large.

*Color.*—Pink.

Fruit:

*Maturity when described.*—Firm ripe — July 29th, 1980.

*Date of first picking.*—July 29th, 1980.

*Date of last picking.*—Aug. 8th, 1980.

*Size.*—Uniform. Large. Average diameter axially — 73 mm. Average transversely in suture plane — 69 mm.

*Form.*—Uniform. Symmetrical. Globose — slightly ovoid.

*Suture.*—A shallow inconspicuous line extending from base to beyond apex, with slight depression beyond pistil point.

*Ventral surface.*—Rounded.

*Lips.*—Equal.

*Cavity.*—Rounded. Slightly elongated in suture plane, with suture showing on one side. Average depth — 10 mm. Average breadth — 17 mm.

*Base.*—Rounded.

*Apex.*—Depressed.

*Pistil point.*—Depressed; i.e., disposed within apical depression.

Skin:

*Texture.*—Medium.

*Tenacity.*—Tenacious to flesh.

*Tendency to crack.*—Slight — none in dry season.

*Color.*—Ground Color — Yellow. Blush Color — Red (Plate 15 — No. 345 — Buccaneer).

*Down.*—Wanting.

Flesh:

*Color.*—Yellow (Plate 7 — No. 148 — Golden Rapture) streaked with red (Plate 15 — No. 345 — Buccaneer). Surface of pit cavity: Red.

*Amygdalin.*—Wanting.

*Juice.*—Moderate.

*Texture.*—Soft. Fine. Melting.

*Fibers.*—Few. Fine. Tender.

*Ripens.*—Evenly.

*Flavor.*—Acid. Mild. Delicate.

*Aroma.*—Wanting.

*Eating quality.*—Best.

Stone:

*Type.*—Free.

*Fibers.*—Short. Free.

*Size.*—Medium.Average length — 40 mm. Average breadth — 27 mm. Average thickness — 22 mm.

*Form.*—Elliptical.

*Base.*—Straight.

*Hilum.*—Oval.

*Apex.*—Slightly acuminate.

*Sides.*—Equal.

*Surface.*—Regularly furrowed toward apex. Ridged toward apex. Pitted from base to above center.

*Ridges.*—Rounded.

*Pits.*—Elongated.

*Ventral edge.*—Thin, with wing toward base.

*Dorsal edge.*—Full, with deep, narrow groove throughout.

*Color.*—Brown (Plate 14 — No. 313 — Congo).

*Tendency to split.*—Slight in dry season.

Use: Market.

Keeping quality: Good.

Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, characterized by late-ripening, freestone fruit in harvest approximately with the clingstone fruit of the Late Le Grand.

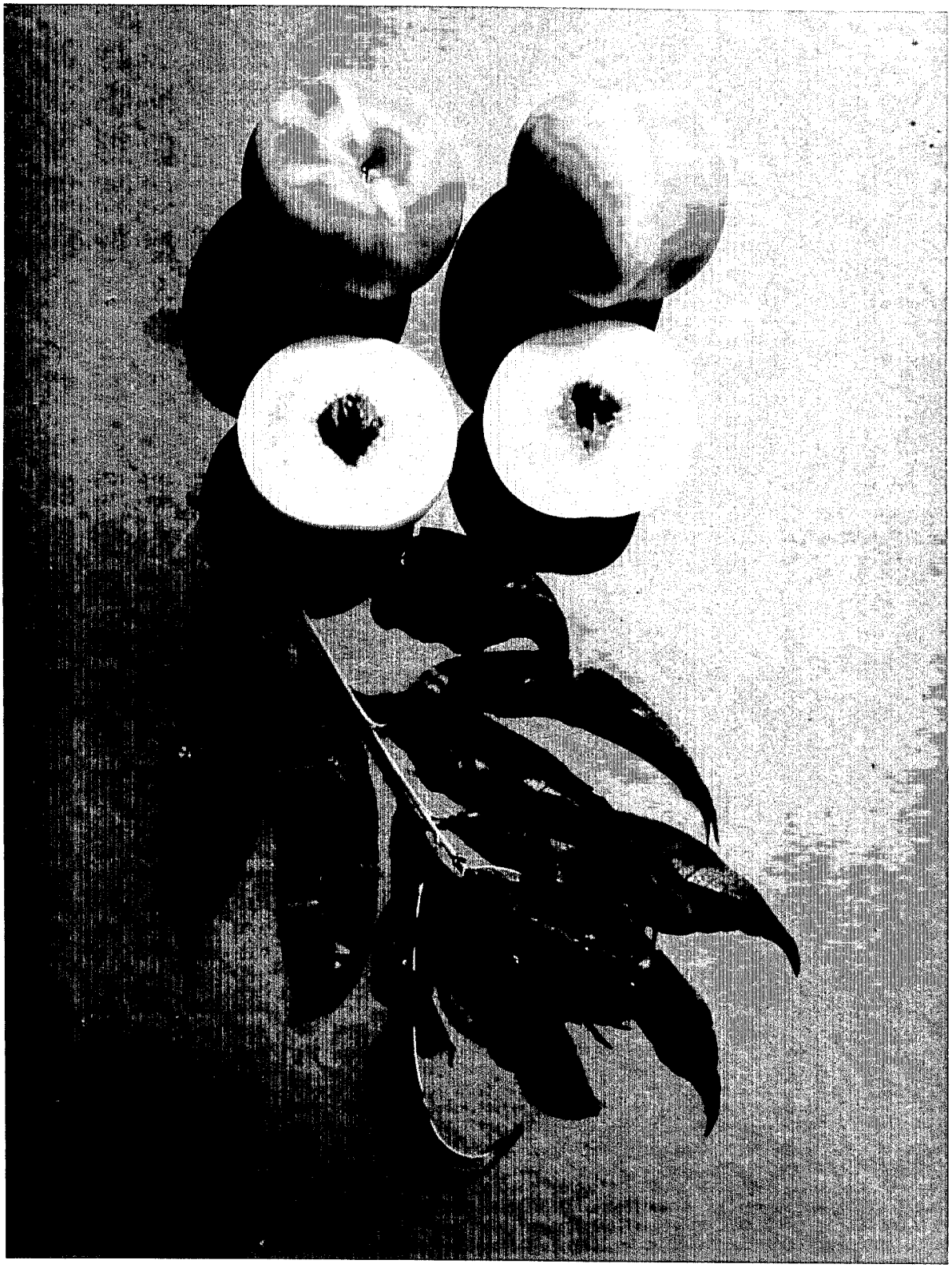

* * * * *